US005131410A

United States Patent [19]

Neill et al.

[11] Patent Number: 5,131,410

[45] Date of Patent: Jul. 21, 1992

[54] ADJUSTABLE BACK SUPPORT FOR RELIEF OF BACK PAIN

[76] Inventors: William R. Neill; Billie C. Neill, both of P.O. Box 8180, Santa Cruz, Calif. 95061-8180

[21] Appl. No.: 829,967

[22] Filed: Feb. 3, 1992

[51] Int. Cl.[5] ........................ A61G 15/00; A61F 5/00

[52] U.S. Cl. ........................ 128/845; 602/36; 606/240

[58] Field of Search ........................ 602/23, 24, 32, 33, 602/34, 35, 38, 39, 40; 269/328; 297/230, 284; 128/845, 870; 606/237, 240

[56] References Cited

U.S. PATENT DOCUMENTS

| | | | |
|---|---|---|---|
| 1,296,722 | 3/1919 | Washburn | 602/39 |
| 3,481,331 | 12/1969 | Carr | 602/24 |
| 3,750,659 | 8/1973 | Loomans | 602/23 |
| 3,896,787 | 7/1975 | Withers | 128/845 |
| 4,133,307 | 1/1979 | Ness | 602/32 |
| 4,362,334 | 12/1982 | Ross | 297/230 |
| 4,457,302 | 7/1984 | Caspari | 128/882 |
| 4,495,943 | 1/1985 | Kurtz | 602/23 |
| 4,549,540 | 10/1985 | Caspari | 128/882 |
| 4,581,754 | 4/1986 | Donovan | 128/845 |
| 5,081,665 | 1/1992 | Kostich | 128/845 |

*Primary Examiner*—Michael A. Brown
*Attorney, Agent, or Firm*—Jeffrey A. Hall

[57] ABSTRACT

An adjustable back support device comprising a base member having two lateral and two traverse edges, a pair of support elements adjustably secured to the base member in a position substantially adjacent to the traverse base member edges to constitute a receiving channel to receive at least the lumbar portion of a human back. Each support element includes a sling angularly secured to a vertical member, a support member which is adjustably secured to the base member, and a pair of receiving slots in the support member. The base member includes a pair of adjustment slots for adjusting the position of the support elements on the surface of the base member.

17 Claims, 2 Drawing Sheets

ADJUSTABLE BACK SUPPORT FOR RELIEF OF BACK PAIN

BACKGROUND OF THE INVENTION

1. Field of Invention

The present invention relates generally to devices and aids for relieving back pain, and particularly to devices for relief of lower back ailments, reducing tension of the back, and relieving stresses and strains of the back.

2. Description of the Prior Art

Heretofore, various devices and aids have been proposed and implemented to relieve back pain and associated ailments. Numerous types of back braces, belts, and other support wear are presently or have been previously available. Often, however, back pain is associated with misaligned vertebra of the spine which result in pinched nerves and the like. Such misalignment has often, in the past, required medical or chiropractic treatments with many devices proposed for such treatments.

Prior art patents known to applicant are U.S. Pat. Nos. 1,294,393, 1,562,266, 2,970,592, 306,287, 3,542,421, 3,901,222, 4,161,337, 4,230,099, 4,352,334, and 4,785,801. None of these devices, however, provide an adjustable back support which is readily adjustable in multiple positions, which is made with a minimum of parts and simple to manufacture and use, and which can be safely used by a layperson without medical or

SUMMARY OF THE INVENTION

Accordingly, the present invention provides a novel device to relieve lower back pain and discomfort and provides the user with multiple positioning choices to assure maximum relief and comfort. A further object of the invention is to provide an adjustable device which can be manufactured very economically, which is comprised of a minimum of parts, and which can be assembled with a minimum of skill and effort. A still further object is to provide a device to relieve back pain and ailments which is effective, reliable, and may be safely used by a layperson without medical or chiropractic supervision.

To achieve these and other objects and advantages the present invention provides an adjustable back support device for the relief of back pain comprising a base member having two lateral and two traverse edges, a pair of support elements adjustably secured to the base member in a spaced relationship positioned substantially adjacent to the traverse base member to constitute a receiving channel to accommodate at least the lumbar portion of a human back. Each support element includes a sling angularly secured to a vertical member, a support member which is adjustably secured to the base member, and means for extending and altering the size and angularity of the sling so as to accommodate different sizes and shapes of users. The spaced relationship and positions of the support elements on the base member may be adjusted by means of a pair of adjustment slots and securing bolts. To further secure and position the support elements and to prevent slippage of the support elements during use an abrasive element is secured to the underside of the support elements and secured thereto and to the base member by an adhesive.

Further objects and advantages of the invention will be apparent from a consideration of the ensuing description and the accompanying drawings.

DETAILED DESCRIPTION OF THE PREFERED EMBODIMENT

Figure 1:
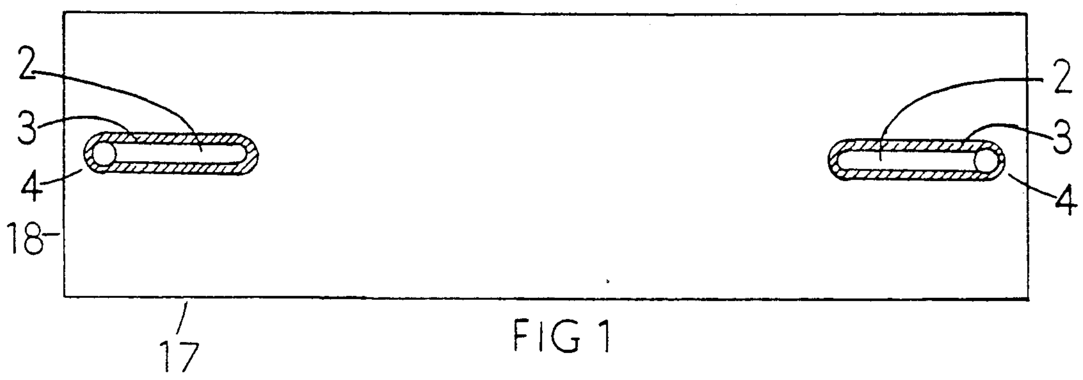
FIG. 1 shows a bottom view of an adjustable support for relief of back pain according to the invention.

The present invention comprises an adjustable back support for relief of back pain, stress, and other ailments and in the preferred embodiment comprises a base member 1 having two lateral edges 17 and two traverse edges 18. A pair of support elements 20 are adjustably secured to base member 1 in a spaced relationship and positioned substantially adjacent to the traverse member edges 18 so as to constitute a receiving channel 19 which receives and conforms to at least the lumbar portion of a human back.

Each support element 02 includes a sling 6 which is angularly secured to a vertical member 9 preferably by staples 13, however, screws, rivets, adhesives, or other conventional fastening means well known in the art may also be used. A support member 10 is adjustably secured to the base member 1 and a pair of adjustment slots 2 in base member 1 provide a means for adjusting the spaced relationship of the pair of support elements 20 in relation to each other on base member 1.

Slippage of support elements 20 is prevented by attaching an abrasive element 16 between support member 10 and base member 1. The abrasive element may be any durable, abrasive material, such as leather, sandpaper, emory cloth, felt, burlap, or the like, and is preferably attached by an adhesive 15, but may be otherwise.

Figure 2:
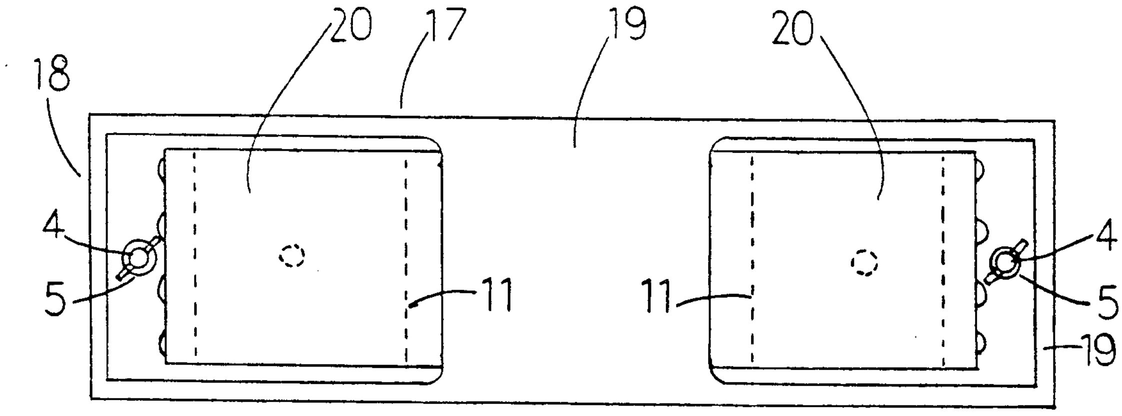
FIG. 2 shows a top view of such adjustable support according to the invention.

Referring now to FIG. 1 a bottom view of the adjustable back support of the present invention is illustrated showing the adjustment slots 2 for support element 02, and a shoulder relief 3 provided for adjusting bolt 4 to set into so that the adjustable back support lies flat on a supporting surface. FIG. 2 shows a top view of the adjustable back support according to the preferred embodiment of the invention with support elements 20, adjusting bolt 4 with wingnut and washer 5, and relief cut 11 provided in the base of support element 20, allowing the adjustable back support to set flat upon base member 1.

Figure 3:
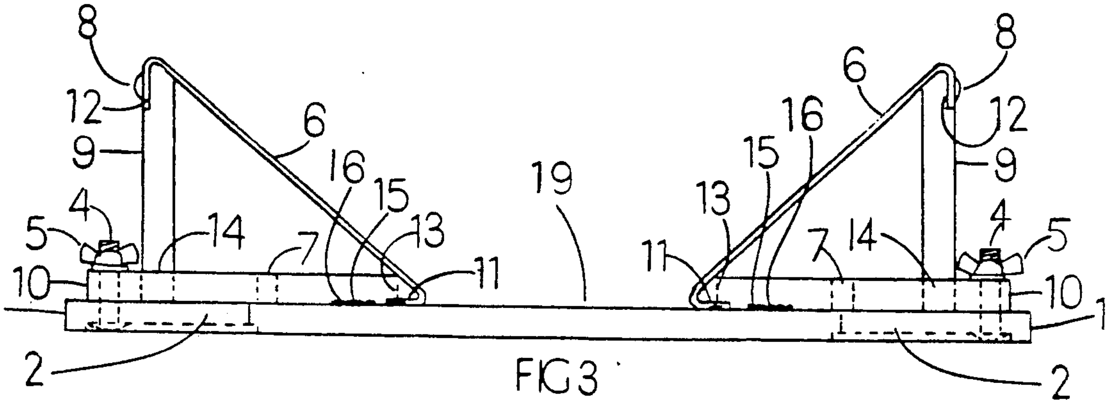
FIG. 3 shows a side view of such adjustable support with the slings in position for use.

In reference now to FIG. 3, illustrating a side view of the adjustable back support and showing the pair of support elements 20 fastened to base member 1 with bolt 4, and wingnut and washer 5. Sling 6 is preferably angularly secured to base member 1 by staples 13. Sling 6 is preferably composed of leather, however, any other durable, flexible material may be used such as cloth, plastic, urethane, or the like. An extension hole 7 is provided to allow sling 6 to adjust to spread the receiving channel 19 to greater width to accommodate different sizes of people. Sling 6 is preferably secured within extension hole 7 by a mechanical fastening means such as staple 13 or any other fastener well known in the art. Screws 8, four in the preferred embodiment, and trim washers, hold sling 6 to vertical member 9, however, rivets, adhesives, nails, pins, or other conventional fastening means well known in the art may be used. A support member 10 having receiving slot 14 adapted to receive and secure vertical member 9 to base member 1 is shown. A relief cut 12 is preferably provided on vertical member 9 of support element 20.

Figure 4:
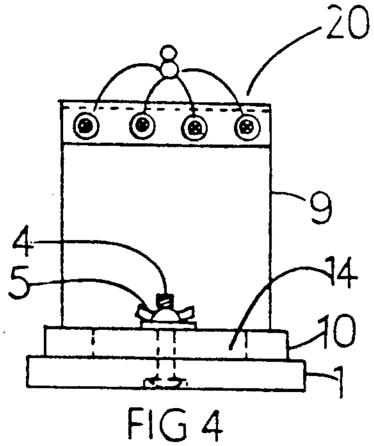
FIG. 4 shows an end view of such adjustable support.

Referring now to FIG. 4, an end view of the adjustable back support is illustrated showing base member 1, support member 10 with receiving slot 14 for vertical element 9 of support element 20, and bolt 4 with wingnut and washer 5, according to the preferred embodiment of the invention.

Figure 5:
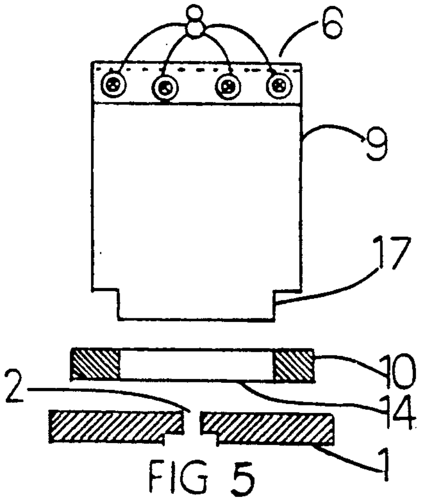
FIG. 5 shows such an adjustable support disassembled, showing the base member, vertical member, and support member, according to the invention.

In FIG. 5, a cut 17 is shown preferably made on vertical member 9 allowing the vertical member 9 to fit within receiving slot 14 of support member 10. Base member 1 is shown with adjustment slot 2 for receiving bolt 4 so that vertical element 9 can be easily adjusted into a desired position on base member 1.

In operation and use the adjustable back support of the present invention provides a very reliable, effective, safe, and easy to use device for relieving back pains, reducing tension of the back, alleviating stress and strain of the back, and for promoting a wide variety of other therapeutic functions. The user simply places the adjustable back support on a supporting surface, adjusts the pair of support elements 20 to a desired spacing, and secures the support elements 20 in place with bolt 4 and wingnut and washer 5. The user then places his or her back in to receiving channel 19 and relief and treatment is commenced.

While the above description contains many specificities they should not be construed as limitation on the scope of the invention but merely as preferred embodiments thereof. Those skilled in the art will envision many other possible variations are within its scope. Accordingly, the scope of the invention should be determined by the appended claims and their legal equivalents, and not by the examples which have been given.

I claim:

1. An adjustable back support device for the relief of back pain, comprising:

a base member having two lateral and two traverse edges, a pair of support elements adjustably secured to said base member in a spaced relationship positioned substantially adjacent to the traverse base member edges to constitute a receiving channel to receive at least the lumbar portion of the back; each support element includes a sling angularly secured to a vertical member, a support member which is adjustably secured to the base member, and means for extending and altering the size and angularity of said sling, means for adjusting the spaced relationship of said pair of support elements on the base member, and means for preventing slippage of said pair of support elements.

2. The adjustable back support device of claim 1 wherein said support element is adjustably secured to said base member by a bolt.

3. The adjustable back support device of claim 1 wherein said sling is angularly secured to said vertical member by screws.

4. The adjustable back support of claim 1 wherein said sling is secured to said support member by staples.

5. The adjustable back support of claim 1 wherein said sling is composed of leather.

6. The adjustable back support of claim 1 wherein said sling is composed of cloth.

7. The adjustable back support of claim 1 wherein said sling is composed of plastic.

8. The adjustable back support of claim 1 wherein said means for adjusting the spaced relationship of said pair of support elements on said base member comprises a pair of adjustment slots in said base member.

9. The adjustable back support device of claim 1 wherein said means for preventing slippage of said pair of support elements comprises an abrasive element attached under each of said support elements by an adhesive.

10. The adjustable back support device of claim 1 wherein said support member further includes a pair of receiving slots adapted to receive and secure said vertical members.

11. A device for being positioned beneath the back of a person lying supine on a supporting surface for relief of back pain, comprising:

a base member having two lateral and two traverse edges, a pair of support elements adjustably secured to said base member in a spaced relationship positioned substantially adjacent to the transverse base member edges to constitute a receiving channel to receive at least the lumbar portion of the back; each support element includes a sling angularly secured to a vertical member, a support member which is adjustably secured to the base member, and means for extending and altering the angularity of said sling, a slotted adjustment means for adjusting the spaced relationship of said pair of support elements on the base member, means for preventing slippage of said pair of support elements.

12. The device of claim 11 wherein said support element is adjustably secured to said base element by a bolt.

13. The device of claim 11 wherein said sling is angularly secured to said vertical member by screws.

14. The device of claim 11 wherein said sling member is composed of leather.

15. The device of claim 11 wherein said slotted adjustment means for adjusting the spaced relationship of said pair of support elements comprises a pair of adjustment slots in said base member.

16. The device of claim 11 wherein said means for preventing slippage of said support element comprises an abrasive element secured by an adhesive to said base member.

17. The device of claim 11 wherein said support member further includes a pair of receiving slots adapted to receive and secure said vertical member

* * * * *